United States Patent [19]

de Ruiter

[11] Plant 4,493

[45] Jan. 15, 1980

[54] ROSE PLANT

[75] Inventor: Gijsbert de Ruiter, Hazerswoude, Netherlands

[73] Assignee: Jackson & Perkins Company, Medford, Oreg.

[21] Appl. No.: 940,855

[22] Filed: Sep. 8, 1978

[51] Int. Cl.[2] ..... A01H 5/00

[52] U.S. Cl. ..... Plt./8

[58] Field of Search ..... Plt./8

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

A heavily branched, bushy rose plant of the miniature class, characterized particularly by its abundance and continuity of blooms, leaflets of a long oval shape, its strong resistance to rose powdery mildew, with little or no fragrance.

11 Drawing Figures

BACKGROUND OF THE INVENTION

The present invention relates to a new and distinct variety of rose plant of the miniature class which was originated by me by crossing the variety Rosy Jewel with pollen of the variety Zorina.

The primary objective of this breeding was to produce a rose variety of the miniature type with an abundance of white blooms on a plant of vigorous, although miniature, growth.

This objective was fully achieved along with other desirable improvements as evidenced by the following unique combination of characteristics which are outstanding in the new variety and which distinguish it from its parents as well as from all other varieties of which I am aware:

1. A heavily branched, bushy plant habit of the miniature class.
2. A strong resistance to rose powdery mildew.
3. An abundance and continuity of blooms.
4. Leaflets of a long oval shape.
5. Light yellow buds (Wilson's Chrome Yellow) opening to white open flowers.
6. Little or no fragrance.
7. Older petal edges curled under when bloom is fully open.

Asexual reproduction of this new variety by budding and cuttings as performed at Hazerswoude, Holland, and at Irvine, Calif., shows that the aforementioned characteristics come true to form and are established and transmitted through succeeding propagations.

The accompanying illustration shows typical specimens of the vegetative growth and flowers of this new variety in different stages of development and as depicted in color as nearly true as it is reasonably possible to make the same in a color illustration of this character.

The following is a detailed description of my new rose cultivar with color in terminology in accordance with Wilson's Horticultural Color Chart except where ordinary dictionary significance of color is indicated.

Parentage:

*Seed parent.*—Rosy Jewel.

*Pollen parent.*—Zorina.

Classification:

*Botanical.*—Rosa hybrid.

*Commercial.*—Miniature.

FLOWER

Observations made from specimens grown at Irvine, Calif., in May, 1978.

Blooming habit: Continuous.

Bud:

*Size.*—½ inches when petals start to unfurl.

*Form.*—Long, pointed ovoid.

*Color.*—When sepals first divide, near Chrome Yellow (605/3), quickly fading to white; when half blown, upper side of petals near white to Chrome Yellow (605/3); lower side of petals, same as upper side.

*Sepals.*—Color: outer surface Scheeles Green (860/3); center area near midrib lighter; inner surface same, very lightly tomentose; three appendaged sepals, normally appendaged; two unappendaged sepals, hairy edged.

*Receptacle.*—Color: Scheeles Green (860/3). Shape: funnel. Size: large, in relation to size of flower. Surface: smooth.

*Peduncle.*—Length: long. Surface: glandular. Color: light green. Strength: bending, slender.

*Opening.*—Outer petals roll back. All petals curl quill-like when fully open.

Bloom:

*Size.*—Medium. Average open size 2".

*Borne.*—In irregular clusters.

*Stems.*—Medium, slender.

*Form.*—Flat when first open. Permanence: all petals curl, quill fashion.

*Petalage.*—Number of petals under normal conditions: 50.

*Color.*—Center of flower: upper side of petals near white to Chrome Yellow (605/3). Reverse side of petals near white to Chrome Yellow (605/3). Base of petals slightly more Chrome Yellow. General tonality from a distance white.

*Variegations.*—None.

*Discoloration.*—General tonality at end of third day: becomes whiter each day.

*Fragrance.*—Slight.

Petals:

*Texture.*—Thin.

*Shape.*—Long, oval.

*Form.*—Moderately quilled edges.

*Arrangement.*—Informal. Petaloids in center, few.

*Persistence.*—Drop off cleanly.
*Lastingness.*—On the plant, long. As cut flower, long.

Reproductive parts:
*Stamens, anthers.*—Small, many. Color, yellow. Arrangement, regular around styles.
*Filaments.*—White.
*Pollen.*—Gold yellow.
*Styles.*—Color: white.
*Stigmas.*—Color: white.

PLANT

Form: Miniature bush.
Growth: Very vigorous, branching, compact.
Foliage: Number of leaflets on normal mid-stem leaves: 5 or 7.
*Size.*—Medium.
*Quantity.*—Abundant.
*Color.*—New foliage: ligher than Spinach Green (0960/3) with a light overlay of Garnet Brown (00918/3) on newly unfolding foliage. Old foliage: near Spinach Green (0960/3).

Leaflets:
*Shape.*—Long, oval pointed.
*Texture.*—Leathery.
*Edge.*—Serrated.

*Serrations.*—Single, small.
*Petiole.*—Rachis: Color, green; underside, prickles.
*Stipules.*—Long, bearded.
*Disease resistance.*—Resistant to mildew under normal growing conditions at Irvine, Calif.

Wood:
*New wood.*—Color: light green. Bark: smooth.
*Old wood.*—Color: green. Bark: smooth.

Prickles:
*Quantity.*—On main stalks from base, few. On laterals from stalk, few.
*Form.*—Narrow base, long, hooked slightly downward.
*Color when young.*—Brown.
*Position.*—Irregular.

Small prickles: None.

I claim:

1. A new and distinct variety of rose of the miniature class, substantially as herein illustrated and described, characterized particularly as to novelty by the unique combination of its vigorous well-branched habit of growth, its long oval leaflets which are resistant to rose powdery mildew, its abundant continuous production of light yellow buds which age to white and are nearly scentless.

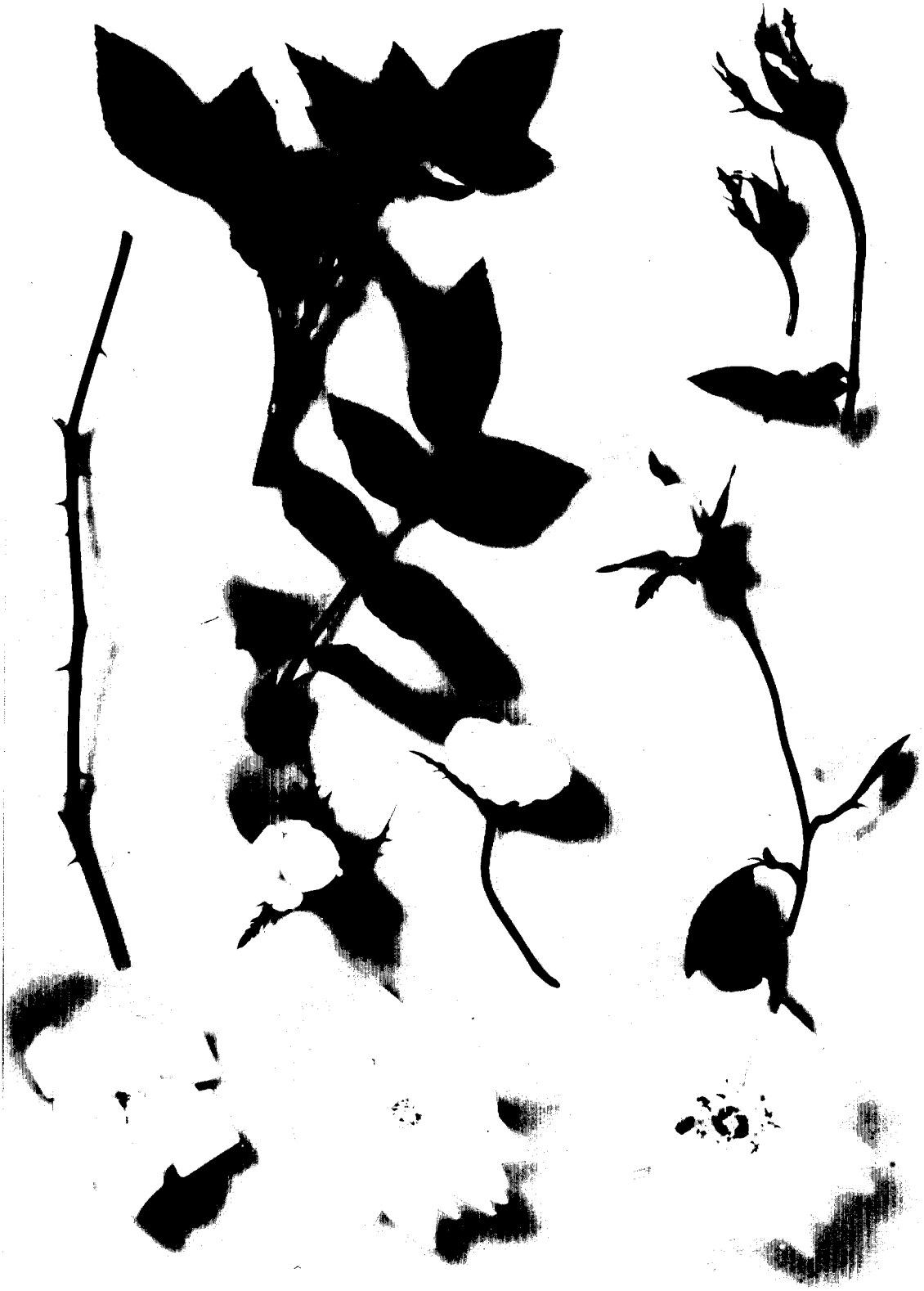

* * * * *